United States Patent [19]

Allgeier

[11] Patent Number: 5,110,818
[45] Date of Patent: May 5, 1992

[54] ANTICONVULSIVE SUBSTITUTED-9-BENZYL-9H-PURINES

[75] Inventor: Hans Allgeier, Lörrach-Haagen, Fed. Rep. of Germany

[73] Assignee: Ciba-Geigy Corporation, Ardsley, N.Y.

[21] Appl. No.: 630,401

[22] Filed: Dec. 19, 1990

Related U.S. Application Data

[63] Continuation of Ser. No. 416,086, Oct. 2, 1989, abandoned.

[30] Foreign Application Priority Data

Oct. 6, 1988 [CH] Switzerland .................. 3731/88

[51] Int. Cl.⁵ .................. A61K 31/52; C07D 473/16
[52] U.S. Cl. .................. 514/261; 514/262; 544/264; 544/265; 544/276; 544/277; 544/326
[58] Field of Search .............. 544/277, 276, 264, 265; 514/261, 262

[56] References Cited

U.S. PATENT DOCUMENTS

| | | | |
|---|---|---|---|
| Re. 31,429 | 10/1983 | Tull et al. | 544/277 |
| 3,846,426 | 11/1974 | Lira et al. | 544/277 |
| 4,189,485 | 2/1980 | Matsuno et al. | 544/277 X |

FOREIGN PATENT DOCUMENTS

| | | |
|---|---|---|
| 108285 | 5/1984 | European Pat. Off. |
| 157637 | 10/1985 | European Pat. Off. |

OTHER PUBLICATIONS

Kelley, et al., J. Med. Chem., 1988, 31, 606-612.
Kelley et al., J. Heterocyclic Chem., 23, 1189-1193 (1986).
Kelly et al., J. Med. Chem., 31, 1005-1009 (1988).
Kelley et al., J. Med. Chem., 31, 2001-2004 (1988).
Kelley et al., J. Med. Chem., 32, 218-224 (1989).
Kelley et al., J. Med. Chem., 29, 1133-1134 (1986).

Primary Examiner—Diana G. Rivers
Attorney, Agent, or Firm—Irving M. Fishman; Karen G. Kaiser

[57] ABSTRACT

The invention relates to novel 9H-purine derivatives, especially to the novel substituted 9-benzyl-9H-purines of the general formula

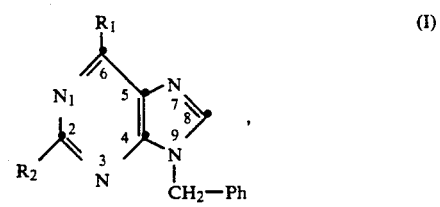

in which Ph is a phenyl radical substituted by halogen, $R_1$ is hydrogen or a free amino group or an amino group that is substituted aliphatically, cycloaliphatically, cycloaliphatically-aliphatically and/or by acyl, and $R_2$ is halogen, lower alkoxy, lower alkyl, a free amino group, or an amino group that is substituted aliphatically, cycloaliphatically, cycloaliphatically-aliphatically and/or by acyl, with the proviso that $R_2$ is other than halogen when Ph is 2-fluorophenyl or 2,5- or 2,6-difluorophenyl and $R_1$ is a radical of the formula $-N(R_{11})(R_{12})$ (Ia) in which either $R_{11}$ is hydrogen, methyl or ethyl and $R_{12}$ is hydrogen, methyl, hydroxymethyl, ethyl, n-propyl, isopropyl, cyclopropyl, cyclopentyl or cyclopropylmethyl, or $R_{11}$ is hydrogen and $R_{12}$ is methoxymethyl, and with the further proviso that $R_2$ is other than chlorine when Ph is 3-chlorophenyl, 4-chlorophenyl or 3,4-dichlorophenyl and $R_1$ is N,N-dimethylamino, and to the novel compounds of formula I in which Ph is 2-fluorophenyl or 2,6-difluorophenyl, $R_1$ is N-methylamino or N,N-dimethylamino and $R_2$ is chlorine, and to the salts thereof in each case. These compounds and the salts thereof can be used as pharmaceutical active ingredients and can be manufactured in a manner known per se.

12 Claims, No Drawings

ANTICONVULSIVE SUBSTITUTED-9-BENZYL-9H-PURINES

This application is a continuation of application Ser. No. 416,086, filed Oct. 2, 1989 now abandoned.

The invention relates to novel 9H-purine derivatives, especially to the novel substituted 9-benzyl-9H-purines of the general formula

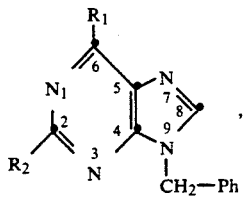

in which Ph is a phenyl radical substituted by halogen, $R_1$ is hydrogen, a free amino group or an amino group that is substituted aliphatically, cycloaliphatically, cycloaliphatically-aliphatically and/or by acyl, and $R_2$ is halogen, lower alkoxy, lower alkyl, a free amino group or an amino group that is substituted aliphatically, cycloaliphatically, cycloaliphatically-aliphatically and/or by acyl, with the proviso that $R_2$ is other than halogen when Ph is 2-fluorophenyl or 2,5- or 2,6-difluorophenyl and $R_1$ is a radical of the formula $-N(R_{11})(R_{12})$ (Ia) in which either $R_{11}$ is hydrogen, methyl or ethyl and $R_{12}$ is hydrogen, methyl, hydroxymethyl, ethyl, n-propyl, isopropyl, cyclopropyl, cyclopentyl or cyclopropylmethyl, or $R_{11}$ is hydrogen and $R_{12}$ is methoxymethyl, and with the further proviso that $R_2$ is other than chlorine when Ph is 3-chlorophenyl, 4-chlorophenyl or 3,4-dichlorophenyl and $R_1$ is N,N-dimethylamino, and to the novel compounds of formula I in which Ph is 2-fluorophenyl or 2,6-difluorophenyl, $R_1$ is N-methylamino or N,N-dimethylamino and $R_2$ is chlorine, and to the salts thereof in each case, to a process for the manufacture of such compouns or their salts, to pharmaceutical preparations containing such compounds or their salts, and to the use of such compounds and their salts. The phenyl radical Ph may have up to and including 3, but preferably 1 or 2, halogen substituents and where it is polysubstituted the substituents may be the same or different. Each of the substituents is bonded preferably in an ortho-position or, less preferably, in a meta-position, but may also be bonded in para-position. The following may be mentioned as examples: 2-halophenyl, also 3- and 4-halophenyl, 2,6-dihalophenyl, also 2,3- and 2,5-dihalophenyl as well as 2,3,6- and 2,5,6-trihalophenyl. 2-Halophenyl and 2,6-dihalophenyl are especially preferred.

Amino groups $R_1$ and $R_2$ that are substituted aliphatically, cycloaliphatically, cycloaliphatically-aliphatically and/or by acyl are, for example, amino groups monosubstituted by an aliphatic, cycloaliphatic or cycloaliphatic-aliphatic radical or by acyl, or amino groups disubstituted by aliphatic, cycloaliphatic or cycloaliphatic-aliphatic radicals, or by an aliphatic radical as well as a cycloaliphatic radical or acyl. Suitable aliphatic radicals are, for example: lower alkyl, lower alkoxy-lower alkyl and hydroxy-lower alkyl; a suitable cycloaliphatic radical is, for example, cycloalkyl; a suitable cycloaliphatic-aliphatic radical is, for example, cycloalkyl-lower alkyl, and a suitable acyl radical is, for example, lower alkanoyl. The following may be mentioned as examples of radicals $R_1$ and $R_2$: amino, N-mono- and N,N-di-lower alkylamino, N-(lower alkoxy-lower alkyl)amino, N-(hydroxy-lower alkyl)amino, N-(hydroxy-lower alkyl)-N-lower alkylamino, N-mono- and N,N-di-cycloalkylamino, N-cycloalkyl-N-lower alkylamino, N-mono- and N,N-di-(cycloalkyl-lower alkyl)-amino, N-(cycloalkyl-lower alkyl)-N-lower alkylamino, N-lower alkanoylamino and N-lower alkanoyl-N-lower alkylamino.

Hereinbefore and hereinafter, unless defined otherwise organic groups and compounds referred to as "lower" preferably contain up to and including 7, especially up to and including 4, carbon atoms (C-atoms).

Halogen is, for example, halogen having an atomic number of up to and including 35, such as fluorine, chlorine or, less preferably, bromine. Lower alkyl is, for example, $C_1$–$C_4$alkyl, such as methyl, ethyl, n-propyl, isopropyl or n-butyl, or also secondary butyl, isobutyl or tertiary butyl, but it can also be a $C_5$–$C_7$alkyl group, i.e. a pentyl, hexyl or heptyl group.

Lower alkoxy is, for example, $C_1$–$C_4$alkoxy, such as methoxy, ethoxy, n-propoxy, isopropoxy or n-butoxy, or also secondary butoxy, isobutoxy or tertiary butoxy, but it can also be a $C_5$–$C_7$alkoxy group, i.e. a pentyloxy, hexyloxy or heptyloxy group.

N-mono-lower alkylamino is, for example, N-$C_1$–$C_7$alkylamino, especially N-$C_1$–$C_4$alkylamino, such as N-methylamino or N-ethylamino.

N,N-di-lower alkylamino is, for example, N,N-di-$C_1$–$C_7$alkylamino, especially N,N-di-$C_1$–$C_4$alkylamino, in each of which the two N-alkyl groups may be the same or different, such as N,N-dimethyl-, N,N-diethyl-, N,N-diisopropyl- or N-butyl-N-methyl-amino.

N-(lower alkoxy-lower alkyl)amino is, for example, N-($C_1$–$C_4$alkoxy-, such as methoxy- or ethoxy-, $C_1$–$C_7$alkyl)amino, especially N-($C_1$–$C_4$alkoxy-, such as methoxy- or ethoxy-, $C_1$–$C_4$alkyl)amino, such as N-(methoxymethyl)-amino or N-(1-methoxyethyl)amino.

N-(hydroxy-lower alkyl)amino is, for example, N-(hydroxy-$C_1$–$C_7$alkyl)-amino, especially N-(hydroxy-$C_1$–$C_4$alkyl)amino, such as N-(hydroxymethyl)-amino or N-(1-hydroxyethyl)amino.

N-(hydroxy-lower alkyl)-N-lower alkylamino is, for example, N-(hydroxy-$C_1$–$C_7$alkyl)-N-$C_1$–$C_7$alkylamino, especially N-(hydroxy-$C_1$–$C_4$alkyl)-N-$C_1$–$C_4$alkylamino, such as N-(1-hydroxyethyl)-N-methylamino or N-(hydroxymethyl)-N-ethylamino.

N-monocycloalkylamino is, for example, N-$C_3$–$C_8$cycloalkylamino, especially N-$C_3$–$C_6$-cycloalkylamino, such as N-cyclopropylamino or N-cyclohexylamino. N,N-dicycloalkylamino is, for example, N,N-di-$C_3$–$C_8$-cycloalkylamino, especially N,N-di-$C_3$–$C_6$-cycloalkylamino, in each of which the two N-cycloalkyl groups may be the same or different, such as N,N-dicyclohexylamino or N-cyclohexyl-N-cyclopropylamino.

N-cycloalkyl-N-lower alkylamino is, for example, N-$C_3$–$C_8$cycloalkyl-N-$C_1$–$C_7$alkylamino, especially N-$C_3$–$C_6$cycloalkyl-N-$C_1$–$C_4$alkylamino, such as N-cyclopropyl-N-methylamino or N-cyclohexyl-N-ethylamino.

N-mono(cycloalkyl-lower alkyl)amino is, for example, N-($C_3$–$C_8$cycloalkyl-$C_1$–$C_7$alkyl)amino, especially N-($C_3$–$C_6$cycloalkyl-$C_1$–$C_4$alkyl)amino, such as N-(cyclopropylmethyl)amino or N-(1-cyclohexylethyl)amino.

N,N-di(cycloalkyl-lower alkyl)amino is, for example, N,N-di($C_3$–$C_8$cycloalkyl-$C_1$–$C_7$alkyl)amino, especially N,N-di($C_3$–$C_6$cycloalkyl-$C_1$–$C_4$alkyl)amino, in each of which the two N-(cycloalkylalkyl) groups may be the same or different, such as N,N-di(cyclopropylmethyl)amino or N-(cyclopropylmethyl)-N-(1-cyclohexylethyl)amino.

N-(cycloalkyl-lower alkyl)-N-lower alkylamino is, for example, N-($C_3$-$C_8$cycloalkyl-$C_1$-$C_7$alkyl)-N-$C_1$-$C_7$alkylamino, especially N-($C_3$-$C_6$cycloalkyl-$C_1$-$C_4$alkyl)-N-$C_1$-$C_4$alkylamino, such as N-(cyclopropylmethyl)-N-ethylamino or N-(1-cyclohexylethyl)-N-methylamino.

Lower alkanoyl is, for example, $C_2$-$C_5$alkanoyl, such as acetyl, propionyl, butyryl, isobutyryl or pivaloyl.

N-lower alkanoylamino is, for example, N-$C_2$-$C_5$alkanoylamino, such as N-acetyl-, N-propionyl-, N-butyryl- or N-pivaloyl-amino.

N-lower alkanoyl-N-lower alkylamino is, for example, N-$C_2$-$C_5$alkanoyl-N-$C_1$-$C_7$alkylamino, especially N-$C_2$-$C_5$alkanoyl-N-$C_1$-$C_4$alkylamino, such as N-acetyl-N-propylamino or N-butyryl-N-methylamino.

The compounds I are able to form salts by way of their basic centres. Salts of compounds I are therefore especially corresponding acid addition salts, preferably pharmaceutically acid acceptable acid addition salts. These are formed, for example, with strong inorganic protonic acids, such as mineral acids, for example sulfuric acid, a phosphoric acid or a hydrohalic acid, with strong organic carboxylic acids, such as lower alkanecarboxylic acids, for example acetic acid, optionally unsaturated dicarboxylic acids, for example malonic, maleic or fumaric acid, or hydroxycarboxylic acids, for example tartaric or citric acid, or with sulfonic acids, such as lower alkanesulfonic or unsubstituted or substituted benzenesulfonic acids, for example methanesulfonic or p-toluenesulfonic acid.

Also included are salts that are unsuitable for pharmaceutical uses, since these can be used, for example, for the isolation or purification of free compounds I and the pharmaceutically acceptable salts thereof.

The novel compounds I and the pharmaceutically acceptable salts thereof have valuable pharmacological properties, especially a pronounced anticonvulsive activity, which may be demonstrated, for example, by way of a marked metrazole antagonism when administered to mice in a dosage range of from approximately 10 mg/kg p.o., and by way of a pronounced protective action against convulsions induced by electric shock when administered to mice and rats in a dosage range of from approximately 8 mg/kg p.o.

The compounds I and the pharmaceutically acceptable salts thereof are accordingly especially suitable for the treatment of convulsions of various origins, for example for the treatment of epilepsy. They can accordingly be used as anticonvulsive, for example anti-epileptic, active ingredients in medicaments. The industrial production of the active substances may also be included.

The invention relates especially to compounds of formula I in which, taking into consideration the afore-mentioned provisos, Ph is a phenyl radical substituted by halogen, $R_1$ is hydrogen, amino, N-mono- or N,N-di-lower alkylamino, N-(lower alkoxy-lower alkyl)amino, N-(hydroxy-lower alkyl)amino, N-(hydroxy-lower alkyl)-N-lower alkylamino, N-mono- or N,N-di-cycloalkylamino, N-cycloalkyl-N-lower alkylamino, N-mono- or N,N-di-(cycloalkyl-lower alkyl)amino, N-(cycloalkyl-lower alkyl)-N-lower alkylamino, N-lower alkanoylamino or N-lower alkanoyl-N-lower alkylamino, and $R_2$ is halogen, lower alkoxy, lower alkyl, amino, N-mono-or N,N-di-lower alkylamino, N-(lower alkoxy-lower alkyl)amino, N-(hydroxy-lower alkyl)amino, N-(hydroxy-lower alkyl)-N-lower alkylamino, N-mono- or N,N-di-cycloalkylamino, N-cycloalkyl-N-lower alkylamino, N-mono- or N,N-di-(cycloalkyl-lower alkyl)amino, N-(cycloalkyl-lower alkyl)-N-lower alkylamino, N-lower alkanoylamino or N-lower alkanoyl-N-lower alkylamino, and to the novel compounds of formula I in which Ph is 2-fluorophenyl or 2,6-difluorophenyl, $R_1$ is N-methylamino or N,N-dimethylamino, and $R_2$ is chlorine, and the salts thereof in each case.

The invention relates especially to compounds of formula I in which, taking into consideration the afore-mentioned provisos, Ph is 2-, 3- or 4-halophenyl, such as 2-fluoro-, 3-fluoro-, 4-fluoro- or 2-chloro-phenyl, 2,3-, 2,5- or 2,6-dihalophenyl, such as 2,3-, 2,5- or 2,6-difluorophenyl or 6-chloro-2-fluorophenyl, or 2,3,6- or 2,5,6-trihalophenyl, such as 2,3,6-trifluorophenyl or 5-chloro-2,6-difluorophenyl, wherein halogen may in each case be halogen having an atomic number of up to and including 35, $R_1$ is hydrogen, amino, N-$C_1$-$C_4$alkylamino, such as N-methylamino or N-ethylamino, N,N-di-$C_1$-$C_4$alkylamino, such as N,N-dimethylamino, N,N-diethylamino or N-butyl-N-methylamino, N-$C_3$-$C_6$cycloalkylamino, such as N-cyclopropylamino or N-cyclohexylamino, or N-lower alkanoylamino, such as N-acetylamino, and $R_2$ is halogen having an atomic number of up to and including 35, such as chlorine or bromine, $C_1$-$C_4$alkoxy, such as methoxy or ethoxy, $C_1$-$C_4$alkyl, such as methyl or ethyl, amino, N-$C_1$-$C_4$alkylamino, such as N-methylamino or N-ethylamino, N,N-di-$C_1$-$C_4$alkylamino, such as N,N-dimethylamino, N,N-diethylamino or N-butyl-N-methylamino, N-$C_3$-$C_6$-cycloalkylamino, such as N-cyclopropylamino or N-cyclohexylamino, or N-lower alkanoylamino, such as N-acetylamino, and to the novel compounds of formula I in which Ph is 2-fluorophenyl or 2,6-difluorophenyl, $R_1$ is N-methylamino or N,N-dimethylamino, and $R_2$ is chlorine, and the salts thereof in each case.

The invention relates especially to compounds of formula I in which, taking into consideration the afore-mentioned provisos, Ph is 2-halophenyl, such as 2-chloro- or 2-fluorophenyl, or 2,6-dihalophenyl, such as 2,6-difluorophenyl, wherein halogen may in each case be halogen having an atomic number of up to and including 35, $R_1$ is hydrogen, amino, N-$C_1$-$C_4$-alkylamino, such as N-methylamino or N-ethylamino, N,N-di-$C_1$-$C_4$alkylamino, such as N,N-dimethylamino, N,N-diethylamino or N-butyl-N-methylamino, or N-lower alkanoylamino, such as N-acetylamino, and $R_2$ is halogen having an atomic number of up to and including 35, such as chlorine or bromine, amino, N-$C_1$-$C_4$alkylamino, such as N-methylamino or N-ethylamino, or N,N-di-$C_1$-$C_4$alkylamino, such as N,N-dimethylamino, N,N-diethylamino or N-butyl-N-methylamino, and to the novel compounds of formula I in which Ph is 2-fluorophenyl or 2,6-difluorophenyl, $R_1$ is N-methylamino or N,N-dimethylamino, and $R_2$ is chlorine, and the salts thereof in each case.

The invention relates more especially to compounds of formula I in which, taking into consideration the afore-mentioned provisos, Ph is 2-fluorophenyl, 2-chlorophenyl or 2,6-difluorophenyl, $R_1$ is hydrogen, amino, N-$C_1$-$C_4$alkylamino, such as N-methylamino, or N,N-di-$C_1$-$C_4$alkylamino, such as N,N-dimethylamino, and $R_2$ is halogen having an atomic number of up to and including 35, such as chlorine, amino, N-$C_1$-$C_4$alkylamino, such as N-methylamino or N-ethylamino, or N,N-di-C$_1$-C$_4$alkylamino, such as N,N-dimethylamino, and to the novel compounds of formula I in which Ph is 2-fluorophenyl or 2,6-difluorophenyl, R$_1$ is N-methylamino or N,N-di-methylamino, and R$_2$ is chlorine, and the salts thereof in each case.

The invention relates especially to compounds of formula I in which, taking into consideration the aforementioned provisos, Ph is 2-fluorophenyl or 2,6-difluorophenyl, R$_1$ is N-C$_1$-C$_4$alkylamino, such as N-methylamino, or N,N-di-C$_1$-C$_4$alkylamino, such as N,N-dimethylamino, and R$_2$ is halogen having an atomic number of up to and including 35, such as chlorine, amino, N-C$_1$-C$_4$alkylamino, such as N-methylamino or N-ethylamino, or N,N-di-C$_1$-C$_4$alkylamino, such as N,N-dimethylamino, and to the novel compounds of formula I in which Ph is 2-fluorophenyl or 2,6-di-fluorophenyl, R$_1$ is N-methylamino or N,N-dimethylamino, and R$_2$ is chlorine, and the salts thereof in each case.

The invention relates especially to compounds of formula I in which, taking into consideration the aforementioned provisos, Ph is 2-fluorophenyl, R$_1$ is N,N-di-C$_1$-C$_4$alkylamino, such as N,N-dimethylamino, and R$_2$ is halogen having an atomic number of up to and including 35, such as chlorine, amino or N-C$_1$-C$_4$alkylamino, such as N-methylamino or N-ethylamino, and to the novel compound of formula I in which Ph is 2-fluorophenyl, R$_1$ is N,N-dimethylamino, and R$_2$ is chlorine, and the salts thereof in each case.

The invention relates most especially to compounds of formula I in which Ph is 2-fluorophenyl, R$_1$ is N,N-di-C$_1$-C$_4$alkylamino, such as N,N-dimethylamino, and R$_2$ is N-C$_1$-C$_4$alkylamino, such as N-methylamino, and the salts thereof.

The invention relates specifically to the novel compounds of formula I mentioned in the Examples and the salts thereof.

The present invention also relates to a process for the manufacture of a compound I or a salt thereof which is based on techniques that are known per se and comprises, for example, a) in a compound of formula

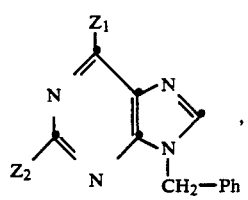

(II)

in which Z$_1$ is a nucleofugal leaving group X$_1$ and Z$_2$ is a nucleofugal leaving group X$_2$ or a radical R$_2$, or in which Z$_1$ is a radical R$_1$ and Z$_2$ is a nucleofugal leaving group X$_2$, or in a tautomer and/or salt thereof, converting Z$_1$ into R$_1$ and/or Z$_2$ into R$_2$, or b) eliminating the compound Y-H from a compound of formula

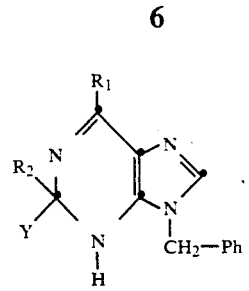

(III)

in which Y is hydroxy, mercapto or unsubstituted or aliphatically substituted amino, or from a tautomer and/or salt thereof, or c) for the manufacture of a compound I in which R$_2$ is amino, or a salt thereof, cyclising a compound of formula

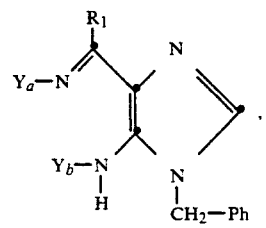

(IV)

in which one of the radicals Y$_a$ and Y$_b$ is cyano and the other is hydrogen, or a tautomer and/or a salt thereof, or d) reacting a compound of formula

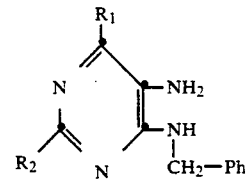

(V)

or a salt thereof with formic acid or a reactive derivative thereof, or e) reacting a compound of formula

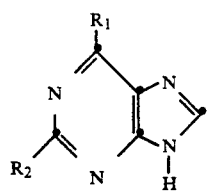

(VI)

or a salt thereof with a compound of formula X$_1$—CH$_2$—Ph (VII), in which X$_1$ is a nucleofugal leaving group, or f) for the manufacture of a compound I in which at least one of the radicals R$_1$ and R$_2$ is amino, or a salt thereof, in a compound of formula

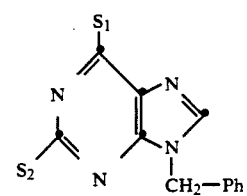

(VIII)

in which $S_1$ is an amino-protecting group and $S_2$ is an amino-protecting group or a radical $R_2$, or $S_1$ is a radical $R_1$ and $S_2$ is an amino-protecting group, or in a salt thereof, converting $S_1$ into $R_1$ and/or $S_2$ into $R_2$, and, if desired, in each case separating an isomeric mixture that may be obtained in accordance with the process into its components and isolating the Isomer of formula I, converting a compound I obtainable according to the process or by another method into a different compound I, converting a free compound I obtainable according to the process into a salt or a salt of a compound I obtainable according to the process into the free compound I or into a different salt of compound I, and/or separating a stereoisomeric mixture that may be obtained according to the process into the stereoisomers and isolating the desired stereoisomer.

The reactions of the process that are described hereinbefore and hereinafter, and also the manufacture of novel starting materials and intermediates, are carried out in a manner known per se. Even if this is not expressly mentioned, the reactions are carried out, analogously to the methods of reaction and formation of known starting materials and intermediates, under the reaction conditions customary in each case, for example as required with cooling, at room temperature or with heating, for example in a temperature range of from approximately $-10°$ C. to approximately $+250°$ C., preferably from approximately 20° C. to approximately 200° C., using the adjuncts that are customary in each case, such as catalysts, condensing agents and solvolysis agents, in the absence or, customarily, in the presence of a suitable solvent or diluent or a mixture thereof, optionally in a closed vessel, in an inert gas atmosphere and/or under anhydrous conditions.

Each of the starting materials of formulae II, III, IV, V, VI, VII and VIII indicated hereinbefore and hereinafter that are used for the manufacture of compounds I and the salts thereof either is known or can be produced by methods that are known per se; the same applies to all other starting materials and intermediates mentioned within the scope of the present description. Starting materials with basic centres, for example the compounds II, III, IV, V and VIII and, where applicable, the tautomers thereof, may also be in the form of salts, such as acid addition salts, preferably with strong inorganic or organic acids, for example analogous to the kind mentioned hereinbefore for acid addition salts of compounds I. The same applies also to all other starting materials and intermediates with basic centres mentioned within the scope of the present description.

Tautomers of compounds II, or salts thereof, may occur, for example, when the groups $Z_1$ and/or $Z_2$ are hydroxy or mercapto. Accordingly, for example, compounds II or salts thereof having enol and/or enthiol partial structures may also be in protomeric form, that is to say in the form of corresponding oxo and/or thioxo tautomers, and/or may be in dynamic equilibrium with those tautomers. The same applies also to all other tautomers of starting materials and intermediates and salts thereof mentioned within the scope of the present description and, in addition, enamine partial structures that may be present may also be in the tautomeric imino form.

Nucleofugal leaving groups $X_1$ and $X_2$ in starting compounds II used in accordance with process variant a) are, for example, optionally etherified or esterified hydroxy or mercapto groups, sulfinyl and sulfonyl groups, or sulfonium groups. Etherified hydroxy is, for example, unsubstituted or substituted phenyl-lower alkoxy, such as unsubstituted or substituted benzyloxy. Esterified hydroxy is especially hydroxy esterified by an organic sulfonic acid, such as unsubstituted or halo-substituted lower alkanesulfonyloxy, for example methanesulfonyloxy or trifluoromethanesulfonyloxy, cycloalkanesulfonyloxy, for example cyclohexanesulfonyloxy, or benzenesulfonyloxy that is unsubstituted or substituted by lower alkyl or by halogen, for example benzenesulfonyloxy, p-bromophenylsulfonyloxy or p-toluenesulfonyloxy, or lower alkanoyloxy, for example acetoxy. Etherified mercapto is, for example, lower alkylthio, such as methylthio, unsubstituted or substituted arylthio, such as unsubstituted or substituted phenylthio or naphthylthio, for example phenylthio, p-tolylthio or naphthylthio, or unsubstituted or substituted aryl-lower alkylthio, such as unsubstituted or substituted benzyl- or naphthyl-methylthio, for example benzylmethylthio, p-bromobenzylmethylthio or naphthylmethylthio. Esterified mercapto groups are, for example, lower alkanoylthio groups, such as acetylthio. Sulfinyl groups are, for example, lower alkanesulfinyl groups, such as methanesulfinyl, unsubstituted or substituted arylsulfinyl groups, such as unsubstituted or substituted benzene- or naphthyl-sulfinyl, for example p-toluene- or naphthyl-sulfinyl, or unsubstituted or substituted benzylsulfinyl, such as benzyl- or p-chlorobenzyl-sulfinyl. Sulfonyl groups are, for example, lower alkanesulfonyl groups, such as methanesulfonyl, unsubstituted or substituted arylsulfonyl groups, such as unsubstituted or substituted benzene- or naphthyl-sulfonyl, for example benzene- or naphthyl-sulfonyl, or unsubstituted or substituted benzylsulfonyl, such as benzyl- or p-methylbenzyl-sulfonyl. Sulfonium groups are, for example, di-lower alkylsulfonium groups, such as dimethylsulfonium. Nucleofugal leaving groups $X_1$ are advantageously also hydroxy groups etherified by a lower alkanol, such as methoxy or ethoxy, or hydroxy groups esterified by a mineral acid, especially halogen, such as chlorine, bromine or iodine.

The conversion of $X_1$ and/or $X_2$ in compounds II, tautomers thereof and their respective salts into radicals $R_1$ and/or $R_2$ is carried out by reaction with compounds of formula H—$R_1$ (IIb) and/or H—$R_2$ (IIj), or if desired with a salt of either, with the removal of compounds $X_1$—H and/or $X_2$—H, the reactions being carried out in customary manner, for example with cooling, at room temperature or with heating, for example in a temperature range of from approximately $-20°$ to approximately $+250°$ C., preferably from approximately $-10°$ to approximately $+200°$ C., optionally in the presence of an inert solvent or diluent or a mixture thereof, optionally in the presence of a water-binding agent, optionally in the presence of a basic agent and/or under an inert gas, such as nitrogen.

Suitable inert solvents or diluents are, for example, water, cyclic ethers, aromatic hydrocarbons, N,N-di-lower alkyl-lower alkanoic acid amides, phosphoric acid lower alkylamides, di-lower alkyl sulfoxides, cyclic amines and, especially, optionally in the form of mixtures with water, lower alkanols, such as tetrahydrofuran, dioxane, benzene, toluene, xylene, N,N-dimethylformamide, hexamethylphosphoric acid triamide, dimethyl sulfoxide, N-methylmorpholine and, especially, optionally in the form of mixtures with water, methanol and ethanol. It is also possible for the manufacture of compounds I in which at least one of the radicals $R_1$ and $R_2$ is an amino group that is unsubstituted or substituted as indicated, or salts thereof, for ammonia or corresponding amines H—R$_1$ (IIb; R$_1$=amino substituted as indicated) and/or H—R$_2$ (IIj; R$_2$=amino substituted as indicated), to be used in excess and employed as solvents or diluents and/or cosolvents, optionally also in dissolved form, for example in the form of aqueous solutions. Similarly it is also possible to use corresponding lower alkanols H—R$_2$ (IIj; R$_2$=lower alkoxy) in excess if only radicals X$_2$ are to be converted into lower alkoxy R$_2$.

Water-binding agents are, for example, oxides of phosphorus, such as phosphorus pentoxide, sulfates of alkali metals or alkaline earth metals, such as sodium or calcium sulfate, halides of alkaline earth metals, such as calcium chloride, or carbodiimides, such as N,N'-dicyclohexylcarbodiimide.

Basic agents are, for example, alkali metal or alkaline earth metal hydroxides, hydrides, amides, lower alkanolates, carbonates, di-lower alkylamides or lower alkylsilylamides, lower alkylamines, optionally N-lower alkylated cycloalkylamines, basic heterocycles, ammonium hydroxides and also carbocyclic amines. The following examples may be mentioned: sodium hydroxide, hydride, amide, methanolate and ethanolate, potassium tert.-butanolate, potassium carbonate, lithium diisopropylamide, potassium bis(trimethylsilyl)amide, calcium hydride, triethylamine, cyclohexylamine, N-cyclohexyl-N,N-dimethylamine, pyridine, benzyltrimethylammonium hydroxide and 1,5-diazabicyclo[5.4.0]undec-5-ene (DBU). For the manufacture of compounds I in which at least one of the radicals R$_1$ and R$_2$ is an amino group that is unsubstituted or substituted as indicated, or salts thereof, there may preferably be used instead of an additional basic agent ammonia or corresponding amines H—R$_1$ (IIb; R$_1$=amino substituted as indicated) and/or H—R$_2$ (IIj; R$_2$=amino substituted as indicated), which in such cases are advantageously employed in excess. In a preferred form of process variant a), for the manufacture of compounds I in which R$_1$ is other than hydrogen, or salts thereof, a compound of formula

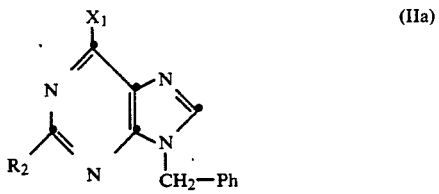

(IIa)

in which X$_1$ is nucleofugal leaving group, preferably hydroxy or halogen, such as chlorine or bromine, or especially for the manufacture of compounds I or salts thereof in which R$_1$ is N,N-di-lower alkylamino, a sulfonyl group, or a tautomer, for example a corresponding 1H—6—oxo compound, and/or a salt thereof is reacted with ammonia or an amine of formula H—R$_1$ (IIb; R$_1$=amino substituted as indicated) or a salt thereof to remove a compound X$_1$—H, the reaction being carried out in customary manner, for example at room temperature or with heating, for example in a temperature range of from approximately 20° to approximately 250° C., optionally in the presence of an inert solvent or diluent, for example of the kind indicated hereinbefore, or a mixture thereof, optionally in the presence of a basic agent, for example of the kind mentioned hereinbefore, optionally in the presence of a water-binding agent, for example of the kind indicated hereinbefore, and/or under an inert gas, such as nitrogen.

In a further preferred form of process variant a), a compound of formula

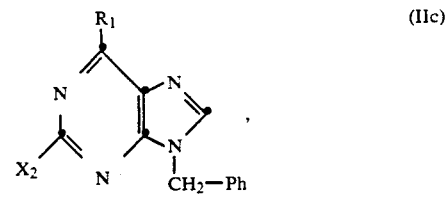

(IIc)

in which X$_2$ is a nucleofugal leaving group, preferably hydroxy or, especially for the manufacture of compounds I or salts thereof in which R$_2$ is N,N-di-lower alkylamino, a sulfonyl group, or a tautomer and/or salt thereof, is reacted with a compound of formula H—R$_2$ (IIj), or a salt thereof, to remove a compound X$_2$—H.

The conversion of X$_2$ in compounds IIc, tautomers thereof and their respective salts into R$_2$ (removal of X$_2$—H) is carried out in customary manner, for example as described hereinbefore for the conversion of compounds IIa, tautomers thereof and their respective salts into compounds I or salts thereof.

In a further preferred form of process variant a), to manufacture compounds I in which R$_1$ is hydrogen, or salts thereof, a compound IIa in which X$_1$ is a nucleofugal leaving group, preferably halogen, such as chlorine or bromine, or optionally etherified mercapto, such as lower alkylthio, for example methylthio, or a tautomer and/or salt thereof, is reduced.

Suitable reducing agents are, for example, Raney nickel (especially for the conversion of optionally etherified mercapto X$_1$ into hydrogen R$_1$) and hydrogen. Reduction with Raney nickel is carried out in customary manner, for example by reacting with a solution of the metal in a lower alkanol, such as methanol, with heating, for example in a temperature range of from approximately 20° to approximately 140° C., preferably from approximately 50° to approximately 100° C. Reduction with hydrogen is advantageously carried out in the presence of a hydrogenation catalyst. Suitable hydrogenation catalysts are, for example, elements of subgroup VIII of the Periodic Table of Elements or derivatives thereof, such as palladium, platinum, platinum oxide, ruthenium, rhodium, a tris(triphenylphosphane)-rhodium(I) halide, for example chloride, or Raney nickel, the catalyst optionally being supported on a carrier, such as activated carbon, an alkali metal carbonate or sulfate or a silica gel. The catalytic hydrogenation is preferably carried out in a polar solvent or diluent, especially in a lower alkanol, such as methanol, or in a strong inorganic acid, such as a hydrohalic acid, for example hydrochloric acid, or a strong organic carboxylic acid, especially aqueous acetic acid or glacial acetic acid, with cooling or heating, preferably in a temperature range of from approximately −10° to approximately +120° C., especially at room temperature. The conversion of optionally etherified mercapto X$_1$ into hydrogen R$_1$ can also be effected by a reaction, carried out in conventional manner, of a corresponding compound IIa with a tri-lower alkyl phosphite, for example triethyl phosphite.

In a further preferred form of process variant a), starting from a compound of formula

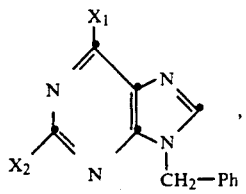

(IId)

in which each of $X_1$ and $X_2$ is a nucleofugal leaving group of the kind described hereinbefore, preferably hydroxy or, especially for the manufacture of compounds I or salts thereof in which $R_1$ and/or $R_2$ are N,N-di-lower alkylamino, a sulfonyl group or, especially for the manufacture of compounds I or salts thereof in which $R_1$ is hydrogen, an optionally etherified mercapto group or, in the case of $X_1$ also halogen, such as chlorine or bromine, or from a tautomer and/or salt thereof, in succession the $X_1$ group may be replaced by an $R_1$ radical and the $X_2$ group may be replaced by an $R_2$ radical. Thus, for example, preferably a compound IId or a tautomer and/or salt thereof may first of all be reacted with ammonia or an amine of formula $H$—$R_1$ (IIb; $R_1$=amino substituted as indicated) or a salt thereof, or, for example, reduced by the action of Raney nickel or by catalytic hydrogenation of the kind described hereinbefore, and the resulting intermediate IIc or a tautomer and/or salt thereof may then be converted into a compound of formula I or into a salt thereof, by reaction with a compound $H$—$R_2$ (IIj) or a salt thereof.

The conversion of $X_1$ and $X_2$ in compounds IId, tautomers thereof and their respective salts into $R_1$ and $R_2$, respectively, is carried out in customary manner, for example as described hereinbefore for the corresponding conversion of compounds IIa and IIc, tautomers thereof and their respective salts into compounds I or salts thereof; the intermediate IIc which is obtained initially from IId does not need to be isolated but is advantageously further reacted in situ, without additional purification, to form a compound I or a salt thereof.

The compounds IIb and IIj and their respective salts are known.

The compounds IId in which $X_1$ and $X_2$ are hydroxy, tautomers and/or salts thereof are also known or can be manufactured analogously to known methods, for example in accordance with process variant e) by reaction of a compound of formula

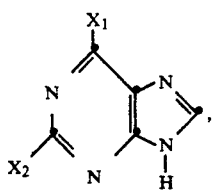

(VI')

in which $X_1$ and $X_2$ are hydroxy, or a tautomer and/or salt thereof with a compound VII.

Compounds IId in which $X_1$ and/or $X_2$ are nucleofugal leaving group other than hydroxy, or tautomers and/or salts thereof, may be obtained by reaction, carried out in conventional manner, of a compound IId ($X_1$=$X_2$=hydroxy) or a tautomer and/or salt thereof with a compound of formula $X_1$—H and/or $X_2$—H in which $X_1$ and $X_2$ are each a nucleofugal leaving group other than hydroxy, for example in the case of $X_1$ preferably halogen or optionally etherified mercapto, it also being possible for halogen leaving groups to be introduced in a manner analogous to that described hereinafter by reaction with a halogenating agent.

The compounds IIa in which $X_1$ is halogen, or tautomers and/or salts thereof, can be manufactured analogously to known methods, for example by reacting a compound of formula

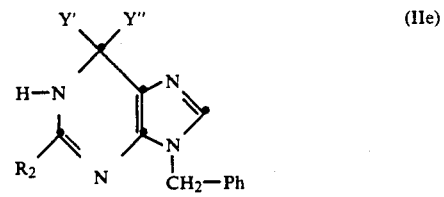

(IIe)

in which $Y'$ and $Y''$ together are optionally functionally modified oxo $X_3$, or a tautomer and/or salt thereof with a halogenating agent. Optionally functionally modified oxo $X_3$ in compounds IIe, tautomers thereof and their respective salts is, for example, thioxo or unsubstituted or substituted imino, but preferably oxo. Unsubstituted or substituted imino is, for example, a group =N—$R_1$, such as imino, N-lower alkylimino, N-cycloalkylimino or N-lower alkanoylimino.

Halogenating agents are, for example, halides of phosphorus or sulfur, such as phosphorus trihalides, phosphorus pentahalides, phosphorus oxytrihalides, thionyl halides or sulfuryl halides, for example phosphorus trichloride, phosphorus tribromide, phosphorus pentachloride, phosphorus oxytrichloride, thionyl chloride or sulfuryl chloride, but may also be, for example, acid halides, such as acid chlorides, of carbonic acid, for example phosgene.

The reaction of a compound IIe or a tautomer and/or salt thereof with a halogenating agent is carried out under customary reaction conditions, for example with heating, for example in a temperature range of from approximately 20° to approximately 200° C., and in an inert solvent, such as a halo-lower alkane, for example tetrachloromethane, but preferably using a solution or suspension of compound IIe or a tautomer and/or salt thereof in an excess of the halogenating agent.

Compounds IIa in which $X_1$ is a nucleofugal leaving group other than halogen, or tautomers and/or salts thereof, can be manufactured in customary manner by further reacting a compound IIa ($X_1$=halogen) or a tautomer and/or salt thereof with a compound $X_1$—H in which $X_1$ is a nucleofugal leaving group other than halogen, preferably optionally etherified mercapto.

The compounds IIc or tautomers and/or salts thereof can be manufactured analogously to known methods from compounds IId or tautomers and/or salts thereof by converting $X_1$ into $R_1$, for example in the manner described hereinbefore.

A compound IIe in which $Y'$ and $Y''$ together are a group $X_3$, preferably oxo, or a tautomer and/or salt thereof can be obtained, for example, by reacting a compound of formula

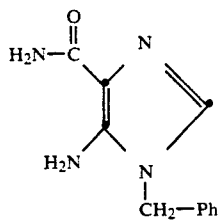

(III)

or a salt thereof with a compound of formula $R_2$—X (IIg), in which X is the functional group of a carboxylic acid or of a functional derivative thereof, for example a carboxy group or a lower alkoxycarbonyl group of the formula —C(=O)—O—Alk in which Alk is lower alkyl, such as methyl, but especially a halocarbonyl group of the formula —C(=O)—Hal in which Hal is halogen, such as chlorine or bromine, or in which X is an amide group of the formula —C(=O)—Am, in which Am is unsubstituted or substituted amino, for example amino, N-lower alkylamino, such as N-methylamino, or N,N-dilower alkylamino, such as N,N-dimethyl- or N,N-diisopropyl-amino, or an orthoester group of the formula —C(O—Alk)$_3$, in which Alk is lower alkyl, such as ethyl, or optionally with a salt thereof, under customary reaction conditions, for example in the presence of a condensing agent, such as a basic agent, and/or with heating, for example in a temperature range of from approximately 20° to approximately 200° C.

It is also possible, in compounds IIa, IIc and IId, for example, first of all to effect a substitution to convert less well suited leaving groups into better suited leaving groups, for example to oxidise lower alkylthio $X_1$ or $X_2$ to lower alkanesulfonyl, or to etherify mercapto $X_1$ or $X_2$ to lower alkylthio, and then to carry out the reaction with the compounds IIb or IIj respectively.

The compounds IIa, IIc and IId, tautomers thereof and their respective salts can also advantageously be produced in a manner analogous to that described under process variant d) by reacting a corresponding compound of formula

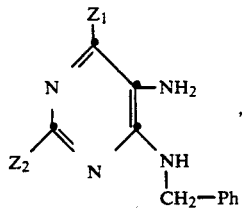

(V')

in which $Z_1$ is a nucleofugal leaving group $X_1$ and $Z_2$ is a nucleofugal leaving group $X_2$ or an $R_2$ radical, or in which $Z_1$ is an $R_1$ radical and $Z_2$ is a nucleofugal leaving group $X_2$, or a salt thereof with formic acid or a reactive derivative thereof in a manner analogous to that described in process variant d).

Unsubstituted or aliphatically substituted amino Y in starting compounds III, tautomers thereof and their respective salts used in accordance with process variant b) is, for example, one of the amino groups indicated hereinbefore in the definition of the radicals $R_1$ and $R_2$, but can also be a different amino group, such as anilino.

The elimination of the compound Y—H from compounds III, tautomers thereof and their respective salts is carried out in customary manner, for example in an inert solvent or diluent, for example of the kind mentioned under process variant a), by heating, for example in a temperature range of from approximately 40° to approximately 250° C., preferably from approximately 80° to approximately 200° C., and/or by treatment with an acid. Acids suitable for that purpose are, for example, mineral acids or anhydrides or acidic salts thereof, for example hydrohalic acids, sulfuric acid, alkali metal hydrogen sulfates, phosphoric acid, polyphosphoric acid, phosphorus pentoxide, phosphorus trichloride or phosphorus oxytrichloride, organic sulfonic acids, such as methanesulfonic acid or p-toluenesulfonic acid, or carboxylic acids or their anhydrides or halides, such as lower alkanoic acids and their anhydrides or halides, for example acetic acid, acetic anhydride or acetyl chloride, and also buffered acid solutions, for example phosphate or acetate buffers, or hydrohalides of nitrogen bases, for example ammonium or pyridinium chloride.

In a preferred form of process variant b), for example a compound III in which Y is hydroxy, or a tautomer and/or salt thereof, is converted into a compound I or a salt thereof by heating at from 100° to 200° C. in an inert solvent, for example a lower alkanoic acid amide, such as acetamide, with the elimination of one equivalent of water. Owing to the fact that the corresponding starting compounds III are readily available, process variant b) is especially suitable for the manufacture of compounds I in which $R_1$ is amino, or the salts thereof. Thus, starting compounds III of this kind, tautomers thereof and their respective salts can be obtained analogously to known methods and are preferably manufactured in situ, for example by cyclising a compound of formula

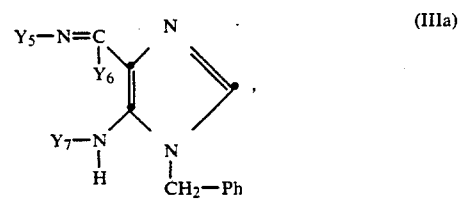

(IIIa)

in which either $Y_5$ and $Y_7$ are hydrogen and $Y_6$ is a group of the formula $R_2$—C(=$X_3$)—NH— (IIIb), or $Y_5$ and $Y_6$ together are an additional bond and $Y_7$ is a group of the formula $R_2$—C(Y)(NH$_2$)— (IIIc), or a tautomer and/or salt thereof, the compound III or a tautomer and/or salt thereof formed as intermediate generally being further reacted in accordance with the invention without being isolated.

In groups of the formula IIIb $X_3$ is optionally functionally modified oxo, such as oxo, thioxo, or unsubstituted or substituted imino, such as imino, N-lower alkylimino, N-cycloalkylimino or N-lower alkanoylimino, or also unsubstituted or substituted N-benzoylimino, N-lower alkanesulfonylimino or N-arylimino.

The cyclisation of compounds IIIa, tautomers thereof, and their respective salts and optionally the subsequent in situ elimination of Y—H from the resulting compounds III or tautomers and/or salts thereof is carried out in customary manner, for example under neutral, acidic or basic conditions, if necessary in the presence of an acid or a basic agent, in the presence of an inert solvent or diluent, at room temperature or, preferably, with heating, for example in a temperature range of from approximately 20° to approximately 250° C., and/or under an inert gas, such as nitrogen. The acids, basic agents and inert solvents or diluents used may be, for example, the corresponding agents mentioned under process variant a). In an especially advantageous manner, however, the inert solvent or diluent may alternatively be a lower alkanoic acid amide, such as acetamide.

In an especially preferred form of process, for example a compound IIIa in which $Y_5$ and $Y_7$ are hydrogen and $Y_6$ is an $R_2$—C(=O)—NH— group (IIIb), or $Y_5$ and $Y_6$ together are an additional bond and $Y_7$ is an $R_2$—C(OH)(NH$_2$)— group (IIIc), or a tautomer and/or salt thereof, is cyclised by heating for several hours, for example in a temperature range of from approximately 80° to approximately 200° C., in a lower alkanoic acid amide, such as acetamide, and a further reaction of the resulting compound III in which Y is hydroxy, or of a tautomer and/or salt thereof, occurs in situ under the reaction conditions to yield the desired end product of formula I or a salt thereof. In an analogous manner corresponding compounds IIIa having groups IIIb in which $X_3$ is imino, or groups IIIc in which Y is amino, or tautomers and/or salts thereof, may be cyclised in an inert solvent, such as a haloalkane, for example tetrachloromethane, and further reacted to form compounds I or salts thereof.

The compounds IIIa, tautomers thereof and their respective salts are obtained from compounds of the formula

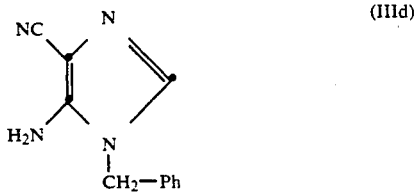

(IIId)

or salts thereof by reaction with a compound of formula $R_2$—C(=$X_3$)—NH$_2$ (IIIe), in which $X_3$ is optionally functionally modified oxo, for example of the kind described for group IIIb, or salts thereof, the operation being carried out analogously to known processes, for example at room temperature or preferably with heating, for example in a temperature range of from approximately 20° to approximately 250° C., under neutral, acidic or basic conditions, if necessary in the presence of an acid or a basic agent, for example of the kind mentioned hereinbefore, in the presence of an inert solvent or diluent, for example of the kind mentioned hereinbefore, and/or under an inert gas, such as nitrogen. The inert solvent or diluent used may be especially a lower alkanoic acid amide, such as acetamide. In an especially preferred form of process a compound IIId or a salt thereof is reacted with a large excess of a compound IIIe ($X_3$=optionally functionally modified oxo, preferably oxo), for example in acetamide ($X_3$=oxo, $R_2$=methyl), with heating, for example in a temperature range of from approximately 80° to approximately 200° C., to form a compound IIIa or a tautomer and/or salt thereof, the reactant IIIe simultaneously acting as solvent or diluent.

Advantageously, however, the compounds IIIa, tautomers thereof and their respective salts are also produced in situ and further reacted, without isolation, to form compounds III or tautomers and/or salts thereof, which in turn are further reacted, in the manner described above, generally also in situ, to form compounds I or salts thereof.

Thus, in the manner of a one-pot reaction, a compound IIId or a salt thereof may be reacted, with heating, with a large excess of a compound IIIe ($X_3$=optionally functionally modified oxo, preferably oxo), for example in acetamide ($X_3$=oxo, $R_2$=methyl), during which reaction first of all a compound IIIa or a tautomer and/or salt thereof is formed, after which cyclisation to form a compound III or a tautomer and/or salt thereof is effected in situ with the continued application of heat, and this in turn is followed by an in-situ elimination of a compound Y—H (Y=hydroxy) to yield a compound I ($R_1$=amino, $R_2$ is, for example, methyl) or a salt thereof.

The cyclisation of starting materials IV used in process variant c), tautomers thereof and their respective salts to compounds I in which $R_2$ is amino, or salts thereof, is carried out under customary cyclisation conditions, for example in a manner analogous to that described in process variant b) for the cyclisation of compounds IIIa to compounds III.

The starting materials IV, tautomers thereof and their respective salts can be obtained analogously to known methods, for example by reaction of a compound of formula

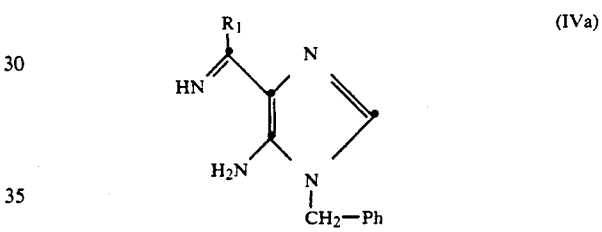

(IVa)

or a tautomer and/or salt thereof with a compound of the formula $X_1$—C≡N (IVb), in which $X_1$ is a nucleofugal leaving group, for example of the kind described in process variant a) for groups $X_1$, preferably halogen, such as chlorine or bromine, or free amino, or amino substituted as indicated for radicals $R_1$ and $R_2$, the reaction being carried out under customary reaction conditions, for example at room temperature or with heating, in an inert solvent or diluent, for example of the kind mentioned hereinbefore, optionally in the presence of a condensing agent, for example a basic agent, for example of the kind described hereinbefore, and/or under an inert gas, such as nitrogen.

In a preferred form of process the compounds IV or tautomers and/or salts thereof are not isolated but are produced in situ and cyclised in accordance with the invention, without isolation or additional purification, to form compounds I or salts thereof.

The compounds IVa, tautomers thereof and their respective salts can be produced analogously to known methods, for example by reaction of a compound IIId or a salt thereof with a compound of formula H—$R_1$ (IIb) or a salt thereof under customary reaction conditions.

Reactive derivatives of formic acid that may be used as starting materials in accordance with process variant d) are, for example, compounds of the formula HC($Y_1$)($Y_2$)($Y_3$) (Va), in which $Y_1$ and $Y_2$ together are optionally functionally modified oxo, for example oxo, thioxo or unsubstituted or substituted imino, such as imino, N-lower alkylimino, N-cycloalkylimino, N-lower alkanoylimino, unsubstituted or substitued N-benzoylimino, N-lower alkanesulfonylimino or N-arylimino, and $Y_3$ is lower alkoxy, such as methoxy, lower alkylthio, such as methylthio, mercapto, halogen, such as chlorine or bromine, or unsubstituted or substituted amino, such as amino, N-lower alkylamino or N,N-di-lower alkylamino, or in which $Y_1$, $Y_2$ and $Y_3$ are each lower alkoxy, such as methoxy or ethoxy, or lower alkylthio, such as methylthio, compounds Va in which $Y_1$, $Y_2$ and $Y_3$ are each methoxy or ethoxy, that is trimethyl and triethyl orthoformate, being especially preferred.

The reaction of a compound V or a salt thereof with formic acid or a reactive derivative thereof is carried out analogously to known procedures under customary reaction conditions, for example in an inert solvent or diluent or in a mixture thereof, at room temperature or with heating, for example in a temperature range of from approximately $+20°$ to approximately $+150°$ C., preferably from approximately $+20°$ to approximately $+100°$ C., optionally in the presence of an acidic agent, for example one of the acids indicated under process variant b), especially an organic sulfonic acid, and/or under an inert gas, such as nitrogen.

Suitable inert solvents and diluents are especially those indicated in process variant a), but it can also be advantageous to carry out the reaction in an excess of the formic acid component, for example in an excess of trimethyl or triethyl orthoformate.

The starting materials V and salts thereof are known or can be manufactured analogously to known methods, for example by reacting a compound of formula

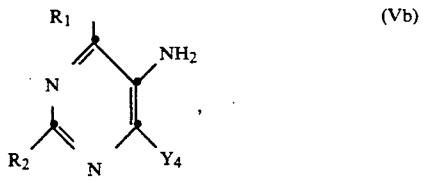

(Vb)

in which $Y_4$ is a nucleofugal leaving group, for example a group $Z_1$ according to process variant a), such as halogen, or a salt thereof with a compound of formula Ph—$CH_2$—$NH_2$ or a salt thereof, the reaction being carried out under the conditions customarily employed, for example as indicated in process variant a).

The derivatives Va and the compounds Vb and salts thereof are known or can be manufactured analogously to known methods. Salts of the starting materials VI used in process variant e) are especially metal salts, such as alkali metal or alkaline earth metal salts, for example sodium, potassium, magnesium or calcium salts, or transition metal salts, for example pharmaceutically acceptable transition metal salts, for example zinc or copper salts, thereof.

Nucleofugal leaving groups $X_1$ in compounds VII are, for example, those of the kind indicated in process variant a) for $X_1$ groups.

The reaction of a compound VI with a compound VII is carried out in customary manner, for example in the presence of a basic condensing agent or, advantageously, by using the component of formula VI in the form of one of its metal salts, at room temperature or, preferably, with heating, for example in a temperature range of from approximately 20° to approximately 200° C., especially from approximately 50° to approximately 150° C., in an inert solvent or diluent, for example of the kind mentioned hereinbefore, optionally in the presence of a phase transfer catalyst, for example a quaternary ammonium salt, such as tetrabutylammonium bromide or benzyltrimethylammonium chloride, or a quaternary phosphonium salt, and/or under an inert gas, such as nitrogen. Suitable basic condensing agents are especially basic condensing agents that form salts with component VI, for example the basic agents mentioned under process variant a). As mentioned, the conversion of component VI into one of its salts is advantageously carried out beforehand, for example, by reaction with one of the mentioned basic agents. Especially suitable are starting materials VI and salts thereof in which $R_1$ and $R_2$ are other than amino or other than amino mono-substituted as indicated.

The starting materials VI are known or can be produced analogously to known methods, for example analogously to process variant a) starting from corresponding compounds II or tautomers and/or salts thereof that carry a hydrogen atom in the 9-position instead of the Ph—$CH_2$ substituent. The starting materials VII are known or can be obtained analogously to known methods. Suitable amino-protecting groups $S_1$ and $S_2$ in a compound VIII used as starting material in accordance with process variant f) or in a salt thereof, and methods for their introduction and removal are known from the State of the Art, which has been elaborated in detail, especially as general methods for the synthesis of peptides [cf. for example, Houben-Weyl: Methoden der Organischen Chemie, 4th Edition, Vol. 15/I and II, E. Wünsch (editor): Synthese von Peptiden (Georg Thieme-Verlag, Stuttgart, 1974)]. Especially suitable are amino-protecting groups of the benzyloxycarbonyl type in which the benzyloxycarbonyl group may be substituted at the aromatic moiety by halogen, lower alkoxy and/or by lower alkyl and especially by nitro, such as the p-chloro- and p-bromobenzyloxycarbonyl, p-methoxybenzyloxycarbonyl, p-methylbenzyloxycarbonyl and especially p-nitrobenzyloxycarbonyl group, or alternatively the isonicotinyloxycarbonyl group, and furthermore ethoxycarbonyl groups that contain in the $\beta$-position a silyl group substituted by three hydrocarbon radicals, such as triphenylsilyl, dimethyl-tert.-butylsilyl or, especially, trimethylsilyl, for example a $\beta$-(tri-lower alkylsilyl)ethoxycarbonyl group, such as $\beta$-(trimethylsilyl)ethoxycarbonyl, and also tert.-butoxycarbonyl groups and analogous groups, and also those of the aralkyl type, such as benzhydryl, di-(4-methoxy)benzhydryl and triphenylmethyl (trityl), or certain aralkoxycarbonyl groups of the 2-(p-biphenylyl)-2-propoxycarbonyl type, which are described in CH-PS 509 266.

The conversion of $S_1$ into $R_1$ and/or $S_2$ into $R_2$, that is to say the removal of the amino-protecting group(s) $S_1$ and/or $S_2$, is carried out in customary manner, for example in the manner dealt with in detail in the mentioned literature, for example by solvolysis, such as mild hydrolysis, for example treatment with water under neutral or weakly acidic conditions, for example by the action of dilute-aqueous mineral or carboxylic acids, for example dilute hydrochloric or acetic acid, by the action of fluoride ions, for example by means of an alkali metal fluoride, or by reduction, for example in accordance with the reduction conditions indicated in process variant a). The compounds VIII and salts thereof can be obtained, for example, analogously to process variants a) to e) by starting from starting materials II, IIb, IIj, III, IV, V and VI obtainable in customary manner which, instead of the amino groups $R_1$ and $R_2$, have an amino-protecting group $S_1$ or $S_2$.

If necessary, when carrying out the reactions of the process in accordance with process variants a) to e), amino groups $R_1$ and/or $R_2$ may also be in temporarily protected form, for example in the form of amino-protecting groups $S_1$ and/or $S_2$. The introduction and removal of such groups $S_1$ and/or $S_2$ is carried out, for example, in accordance with the conditions indicated in process variant f).

If desired, a reaction according to the process can also be combined with the removal of the amino-protecting group(s) $S_1$ and/or $S_2$, for example the conversion of an optionally etherified mercapto group $X_1$ into hydrogen $R_1$ in accordance with process variant a) can be combined with the removal of an amino-protecting group $S_2$ in accordance with process variant f).

Compounds of formula I obtainable in accordance with the process or by some other method can be converted into different compounds of formula I by converting one or more variables of the general formula I into other variables.

For example, unsubstituted amino $R_1$ and/or $R_2$ in compounds I can be converted into N-mono- or N,N-di-lower alkylamino, and N-mono-lower alkylamino $R_1$ and/or $R_2$ can be converted into N,N-di-lower alkylamino, for example by treatment with a reactive ester of a lower alkanol, such as a lower alkyl halide, for example a lower alkyl bromide or iodide, a lower alkanesulfonate, for example methanesulfonate, an unsubstituted or substituted arylsulfonate, such as benzenesulfonate or p-toluenesulfonate, or a di-lower alkyl sulfate, for example dimethyl sulfate, preferably under basic conditions, such as in the presence of sodium hydride or of sodium hydroxide solution or potassium hydroxide solution and advantageously in the presence of a phase transfer catalyst, such as tetrabutylammonium bromide or benzyltrimethylammonium chloride. With such a conversion it is possible either to introduce only one N-lower alkyl group or, alternatively, in a single reaction step, to introduce several, especially from 2 up to and including 4, N-lower alkyl groups. It is also possible in successive reaction steps with suitable selection of the lower alkyl components for different N-lower alkyl groups to be introduced into unsubstituted amino or N-mono-lower alkylamino $R_1$ and/or $R_2$. According to this method of N-alkylation, in each case compounds I are obtained in which the N-lower alkyl groups introduced in the same reaction step are all the same.

In analogous manner it is also possible for a N-lower alkyl group to be introduced into N-(hydroxy-lower alkyl)amino, N-monocycloalkylamino, N-mono(cycloalkyl-lower alkyl)amino and N-lower alkanoylamino $R_1$ and/or $R_2$, resulting in N-(hydroxy-lower alkyl)-N-lower alkylamino, N-cycloalkyl-N-lower alkylamio, N-(cycloalkyl-lower alkyl)-N-lower alkylamino and N-lower alkanoyl-N-lower alkylamino $R_1$ and/or $R_2$.

Similarly, with corresponding appropriate modification of the alkylation components it is also possible to convert unsubstituted amino $R_1$ and/or $R_2$ into N-(lower alkoxy-lower alkyl)amino $R_1$ and/or $R_2$ by the introduction of a N-(lower alkoxy-lower alkyl) group, into N-(hydroxy-lower alkyl)amino $R_1$ and/or $R_2$ by the introduction of a N-(hydroxy-lower alkyl) group, into N-mono- or N,N-di-cycloalkylamino $R_1$ and/or $R_2$ by the introduction of one or more, especially from 2 up to and including 4, N-cycloalkyl group(s), or into N-mono- or N,N-di-(cycloalkyl-lower alkyl)amino $R_1$ and/or $R_2$ by the introduction of one or more, especially from 2 up to and including 4, N-(cycloalkyl-lower alkyl) group(s), and also to convert N-lower alkylamino $R_1$ and/or $R_2$ into N-(hydroxy-lower alkyl)-N-lower alkylamino $R_1$ and/or $R_2$ by the introduction of a N-(hydroxy-lower alkyl) group, into N-cycloalkyl-N-lower alkylamino $R_1$ and/or $R_2$ by the introduction of a N-cycloalkyl group, or into N-(cycloalkyl-lower alkyl)-N-lower alkylamino $R_1$ and/or $R_2$ by the introduction of a N-(cycloalkyl-lower alkyl) group, and furthermore to convert N-monocycloalkylamino $R_1$ and/or $R_2$ into N,N-dicycloalkylamino $R_1$ and/or $R_2$ by the introduction of a N-cycloalkyl group as well as to convert N-mono-(cycloalkyl-lower alkyl)amino $R_1$ and/or $R_2$ into N,N-di(cycloalkyl-lower alkyl)amino $R_1$ and/or $R_2$ by the introduction of a N-(cycloalkyl-lower alkyl) group.

Furthermore, unsubstituted amino $R_1$ and/or $R_2$ can be N-acylated, for example converted into N-lower alkanoylamino $R_1$ and/or $R_2$ by reaction with a lower alkanoic acid, such as formic, acetic or propionic acid, or a reactive derivative of such an acid, for example an acid halide, such as an acid chloride, an ester or, especially, an anhydride, for example acetyl chloride or acetic anhydride. Similarly, N-lower alkylamino $R_1$ and/or $R_2$ can be converted into N-lower alkanoyl-N-lower alkylamino $R_1$ and/or $R_2$. In these conversions it is again possible either to introduce only one N-acyl group, or to N-acylate both amino or N-lower alkylamino $R_1$ and amino or N-lower alkylamino $R_2$ in one reaction step. It is also possible by suitable selection of the acylating agents to introduce different N-acyl groups into unsubstituted amino or N-lower alkylamino $R_1$ and $R_2$ in successive reaction steps. In each case compounds I are obtained in which the N-acyl groups that are introduced in the same reaction step are all the same.

Also, N-lower alkanoylamino $R_1$ and/or $R_2$ can be converted into unsubstituted amino $R_1$ and/or $R_2$, for example by reduction, that is exchange of the acyl group(s) for hydrogen, for which purpose customary reduction systems and reaction conditions are suitable, for example diborane, lithium aluminum hydride in tetrahydrofuran, diethyl ether or dioxane, sodium borohydride/cobalt(II) chloride, sodium borohydride/-trifluoroacetic acid or trihalosilanes, such as trichlorosilane. Furthermore, N-lower alkanoylamino $R_1$ and/or $R_2$ can also be converted into unsubstituted amino $R_1$ and/or $R_2$ by hydrolysis, the hydrolysis being carried out under customary reaction conditions, for example in aqueous solution, in the presence of a basic agent, especially, for example, in the presence of an alkali metal hydroxide or lower alkanolate, such as sodium or potassium hydroxide or sodium methanolate, preferably in an organic solvent or diluent or cosolvent and/or with heating, preferably in a temperature range of from approximately 20° to approximately 150° C., especially from approximately 40° to approximately 100° C. In these processes it is possible, depending on the number of equivalents of reducing agent or of basic agent used, to reduce or hydrolyse, respectively, only one or, if present, both, acyl group(s) to unsubstituted amino $R_1$ or $R_2$, as the case may be.

Furthermore, N-mono-lower alkylamino $R_1$ and/or $R_2$ may be converted into unsubstituted amino $R_1$ and-/or $R_2$ by first of all oxidising the N-lower alkyl group in conventional manner to the N-lower alkanoyl group and then converting the latter in the manner indicated into the unsubstituted amino group.

Halogen or lower alkoxy $R_2$ can be converted into different radicals $R_2$ in a manner analogous to that described in process variant a) for the conversion of radicals $Z_1$ and $Z_2$ into $R_1$ and $R_2$ respectively. Similarly, halogen $R_2$ can also be exchanged for lower alkoxy $R_2$.

Depending on the number of asymmetric carbon atoms, the novel compounds of formula I and salts thereof can form stereoisomers, for example diastereoisomers or enantiomers. Asymmetric carbon atoms may occur, for example in compounds I or salts thereof, in corresponding lower alkyl radicals $R_2$.

Resulting mixtures of isomers and mixtures of diastereoisomers may be separated into their components on the basis of the different physical properties thereof by customary physical separating methods, for example by distillation, crystallisation and/or chromatography.

Resulting mixtures of enantiomers, for example racemates, may be resolved according to known methods into the enantiomers, for example by recrystallisation from an optically active solvent, chromatography on chiral adsorbents, with the aid of suitable microorganisms, by cleaving with specific immobilised enzymes, by way of the formation of inclusion compounds, for example using chiral crown ethers, in which process only one enantiomer is complexed, or by conversion into diastereoisomeric salts, for example by reaction of a basic end product racemate with an optically active acid, such as carboxylic acid, for example tartaric or malic acid, or sulfonic acid, for example camphorsulfonic acid, and separation of the diastereoisomeric mixture obtained in this manner, for example on the basis of the different solubilities, into the diastereoisomers from which the desired enantiomer can be freed by the action of suitable agents. Advantageously, the more active stereoisomer is isolated in each case.

Further, resulting free compounds of formula I having basic centres can be converted in a manner known per se into acid addition salts, for example by reacting a solution of the free compound in a suitable solvent or mixture of solvents with one of the afore-mentioned acids or with a solution thereof or with a suitable ion exchanger.

Resulting acid addition salts of compounds of formula I can be converted in a manner known per se into the free compounds, for example by treatment with a base, such as an alkali metal hydroxide, a metal carbonate or hydrogen carbonate, or ammonia, or with a suitable ion exchanger.

Resulting acid addition salts of compounds of formula I can be converted in a manner known per se into different acid addition salts, for example by treatment of a salt of an organic acid with a suitable metal salt, such as a sodium, barium or silver salt, of an acid in a suitable solvent in which the inorganic salt being formed is insoluble and thus separates out from the reaction mixture.

The novel compounds of formula I and salts thereof can also be obtained in the form of their hydrates and/or may include other solvents, for example solvents optionally used for the crystallisation of substances present in solid form.

Depending on the procedure and reaction conditions, the compounds of formula I of the invention may be obtained in free form or in the form of their salts.

Owing to the close relationship between the novel compounds of formula I in free form and in the form of their salts, hereinbefore and hereinafter references to the free compounds of formula I shall, where appropriate, also include the corresponding salts, and references to salts shall, where appropriate, also include the corresponding free compounds of formula I.

The invention relates also to those forms of the process in which one of the compounds obtainable as intermediate at any stage of the process is used as starting material and the remaining steps are carried out, or a starting material is used in the form of a salt or, especially, is formed under the reaction conditions.

The invention relates also to novel starting materials that have been developed specifically for the manufacture of the compounds according to the invention, especially the selection of starting materials resulting in the compounds of formula I referred to at the beginning as being preferred, to processes for the manufacture thereof, and to their use as intermediates.

The invention likewise relates to the use of the novel compounds of formula I and the pharmaceutically acceptable salts thereof, especially as pharmacological, especially anticonvulsively effective, active substances. They may be used, preferably in the form of pharmaceutical preparations, in a method for the prophylactic and/or therapeutic treatment of the animal or human body, especially as anticonvulsants, for example for the treatment of convulsions of various origins, for example for the treatment of epilepsy.

The invention relates also to pharmaceutical preparations that contain a compound of formula I or a pharmaceutically acceptable salt thereof as active ingredient, and to processes for the manufacture thereof.

The pharmaceutical preparations according to the invention are preparations that contain a therapeutically effective amount of the active substance of the invention, optionally together with inorganic or organic, solid or liquid, pharmaceutically acceptable adjuncts, and that are suitable for enteral, for example oral, or parenteral administration to warm-blooded animals. Pharmaceutical preparations in dosage unit forms, such as dragees, tablets, capsules or suppositories and also ampoules, that contain the active ingredient together with diluents, for example lactose, dextrose, saccharose, mannitol, sorbitol, cellulose and/or glycine, and/or lubricants, for example silica, talc, stearic acid or salts thereof, such as magnesium or calcium stearate, and/or polyethylene glycol, are therefore preferably used. Tablets may also contain binders, for example magnesium aluminium silicate, starches, such as corn, wheat, rice or arrowroot starch, gelatin, tragacanth, methylcellulose, sodium carboxymethylcellulose and/or polyvinylpyrrolidone and, if desired, disintegrators, for example starches, agar, alginic acid or a salt thereof, such as sodium alginate, and/or effervescent mixtures, adsorbents, colouring substances, flavourings and/or sweeteners. Also, the novel compounds of formula I may be used in the form of parenterally administrable preparations or in the form of infusion solutions. Such solutions are preferably isotonic aqueous solutions or suspensions, it being possible, for example in the case of lyophilised preparations that contain the active ingredient on its own or together with a carrier, for example mannitol, for these to be prepared before use. The pharmaceutical preparations may be sterilised and/or may contain adjuncts, for example preservatives, stabilisers, wetting agents and/or emulsifiers, solubilisers, salts for regulating the osmotic pressure and/or buffers. The novel pharmaceutical preparations which, if desired, may contain other pharmacologically active substances, are produced in a manner known per se, for example by means of conventional mixing, granulating, confectioning, dissolving or lyophilising processes, and contain from approximately 0.1% to approximately 100%, especially from approximately 1% to approximately 50%, and in the case of lyophilisates up to 100%, active ingredient.

The dosage may depend on various factors, such as mode of administration, species of warm-blooded animal, age and/or individual condition. In the case of oral administration, the daily dose administered is normally from approximately 1 to approximately 30 mg/kg, and in the case of a warmblooded animal weighing approximately 70 kg is preferably from approximately 0.1 g to approximately 3.0 g, it also being possible to administer the daily dose in several partial doses.

The known compounds of formula I, which are covered by the aforementioned provisos, can likewise be used, in a manner analogous to that described hereinbefore, in free form or in the form of pharmaceutically acceptable salts as pharmacological, especially anticonvulsively effective, active substances, for example, preferably in the form of the pharmaceutical preparations described hereinbefore, in any one of the methods of treatment described hereinbefore; the invention relates also to the corresponding uses, methods of treatment, pharmaceutical preparations and processes for the preparation of the latter ones.

The following Examples serve to illustrate the above-described invention but are not intended to limit the scope thereof in any way. Temperatures are in degrees Celsius.

EXAMPLE 1

3.31 g (16.8 mmol) of 2-chloro-6-(N,N-dimethylamino)-9H-purine are dissolved in 60 ml of N,N-dimethylformamide. 4.16 g (30.2 mmol) of potassium carbonate and 2.02 ml (16.8 mmol) of 2-fluorobenzyl bromide are added to the solution. The reaction mixture is then stirred for 3 hours at room temperature and then ice water is added and the whole is extracted three times with dichloromethane. The combined organic phases are washed twice with water, dried over magnesium sulfate and concentrated by evaporation. The residue is chromatographed on silica gel with toluene/ethyl acetate (3:1) as eluant. The eluate is concentrated by evaporation and the residue obtained is recrystallised from ethyl acetate/diethyl ether. In this manner 2-chloro-6-(N,N-dimethylamino)-9-(2-fluorobenzyl)-9H-purine is obtained in the form of colourless needles having a melting range of from 130° to 131°.

The 2-chloro-6-(N,N-dimethylamino)-9H-purine can be obtained, for example, as follows:

Xanthine (2,6-dihydroxy-9H-purine) is converted by reaction with phosphorus oxytrichloride in accordance with G. B. Elion and G. H. Hitchings, J. Am. Chem. Soc. 78, 3508 (1956) into the 2,6-dichloro-9H-purine and the latter is reacted with N,N-dimethylamine in accordance with J. A. Montgomery and L. B. Holum, J. Am. Chem. Soc. 80, 404 (1958) to form 2-chloro-6-(N,N-dimethylamino)-9H-purine.

EXAMPLE 2

2.5 g (8.2 mmol) of 2-chloro-6-(N,N-dimethylamino)-9-(2-fluorobenzyl)-9H-purine (Example 1) and 10 ml of ethanolic N-methylamine solution (16%) are heated for 120 hours at 80° to 85° in an autoclave. The reaction mixture is then concentrated by evaporation under reduced pressure. The residue is taken up in dichloromethane. The dichloromethane phase is washed twice with water, dried over magnesium sulfate and concentrated by evaporation. the residue is chromatographed on silica gel with toluene/ethyl acetate (10:1) as eluant. The eluate is concentrated by evaporation and the residue obtained is recrystallised from dichloromethane/hexane. In this manner 6-(N,N-dimethylamino)-9-(2-fluorobenzyl)2-(N-methylamino)-9H-purine is obtained in the form of colourless needles having a melting point of 100°.

EXAMPLE 3

In a manner analogous to that described in Example 2 it is also possible, using ammonia instead of N-methylamine, to obtain the 2-amino-6-(N,N-dimethylamino)-9-(2-fluorobenzyl)-9H-purine, which has a melting range of from 197° to 198° (methanol/diethyl ether), the reaction mixture being heated for 48 hours at 160°.

EXAMPLE 4

In a manner analogous to that described in Example 2 it is also possible, using N-ethylamine instead of N-methylamine, to obtain the 2-(N-ethylamino)-6-(N,N-dimethylamino)-9-(2-fluorobenzyl)-9H-purine, which has a melting range of from 76° to 77° (dichloromethane/hexane), the reaction mixture being heated for 160 hours at from 90° to 95°.

EXAMPLE 5

In a manner analogous to that described in Example 2 it is also possible, using N,N-dimethylamine instead of N-methylamine, to obtain the 2,6-bis(N,N-dimethylamino)-9-(2-fluorobenzyl)-9H-purine, which has a melting point of 127° (dichloromethane/diethyl ether), the reaction mixture being heated for 24 hours at 140°.

EXAMPLE 6

In a manner analogous to that described in Example 1 it is also possible, using 2-chloro-6-(N-methylamino)-9H-purine instead of 2-chloro-6-(N,N-dimethylamino)-9H-purine, to obtain the 2-chloro-9-(2-fluorobenzyl)-6-(N-methylamino)-9H-purine, which has a melting range of from 169° to 170° (methanol/diethyl ether). The 2-chloro-6-(N-methylamino)-9H-purine can be obtained, for example, by reacting 2,6-dichloro-9H-purine with N-methylamine in a manner analogous to that described in Example 1.

EXAMPLE 7

6.5 g (25.7 mmol) of 5-amino-2-chloro-4-[N-(2-fluorobenzyl)-amino]-pyrimidine are dissolved at room temperature in 65 ml of triethyl orthoformate. 30 mg of methanesulfonic acid are added to the solution and the reaction mixture is then stirred for 15 hours at room temperature. The reaction mixture is then concentrated by evaporation and the residue is chromatographed on silica gel with toluene/ethyl acetate (3:1) as eluant. The eluate is concentrated by evaporation and the residue obtained is recrystallised from dichloromethane/diethyl ether. In this manner 2-chloro-9-(2-fluorobenzyl)-9H-purine is obtained in the form of colourless crystals having a melting range of from 103° to 104°.

The 5-amino-2-chloro-4-[N-(2-fluorobenzyl)amino]-pyrimidine can be obtained, for example, as follows:

A mixture of 0.5 g (3.1 mmol) of 5-amino-2,4-dichloropyrimidine [D. T. Hurst, Heterocycl. 22, 79 (1984)], 0.35 ml (3.1 mmol) of 2-fluorobenzylamine and 0.46 ml (3.4 mmol) of triethylamine in 8 ml of 1-butanol is heated under reflux for 24 hours. The reaction mixture is then cooled to 0°. The resulting beige-coloured suspension is filtered with suction and the filter cake is washed with cyclohexane and suspended in water for 30 minutes at room temperature with stirring. The suspension is again filtered with suction and the filter cake is dried under a high vacuum at 100° over tetraphosphorus decaoxide. In this manner 5-amino-2-chloro-4-[N-(2-fluorobenzyl)amino]-pyrimidine is obtained in the form of beige-coloured crystals having a melting range of from 224° to 225°.

EXAMPLE 8

In a manner analogous to that described in Example 2 it is also possible, by reacting 2-chloro-9-(2-fluorobenzyl)-9H-purine (Example 7) with N-methylamine, to obtain the 9-(2-fluorobenzyl)-2-(N-methylamino)-9H-purine, which has a melting range of from 184° to 185° (methanol/diethyl ether), the reaction mixture being heated for 24 hours at from 80° to 85°.

EXAMPLE 9

In a manner analogous to that described in Example 2 it is also possible, by reacting 2-chloro-9-(2-fluorobenzyl)-9H-purine (Example 7) with N,N-dimethylamine, to obtain the 2-(N,N-dimethylamino)-9-(2-fluorobenzyl)-9H-purine, which has a melting range of from 112° to 113° (methanol/diethyl ether), the reaction mixture being heated for 24 hours at from 80° to 85°.

EXAMPLE 10

In a manner analogous to that described in Example 2 it is also possible, by reacting 2-chloro-9-(2-fluorobenzyl)-6-(N-methylamino)-9H-purine (Example 6) with ammonia, to obtain the 2-amino-9-(2-fluorobenzyl)-6-(N-methylamino)-9H-purine, which has a melting range of from 207° to 208°.

EXAMPLE 11

In a manner analogous to that described in Example 10 it is also possible, by reacting with N-methylamine instead of ammonia, to obtain the 2,6-bis(N-methylamino)-9-(2-fluorobenzyl)-9H-purine, which has a melting range of from 170° to 171°.

EXAMPLE 12

In a manner analogous to that described in Example 10 it is also possible, by reacting with N,N-dimethylamine instead of ammonia, to obtain the 2-(N,N-dimethylamino)-9-(2-fluorobenzyl)-6-(N-methylamino)-9H-purine, which has a melting range of from 180° to 181°.

EXAMPLE 13

In a manner analogous to that described in Examples 1 to 12 it is also possible to obtain the 2,6-diamino-9-(2-fluorobenzyl)-9H-purine.

EXAMPLE 14

In a manner analogous to that described in Examples 1 to 12 it is also possible to obtain the 6-amino-9-(2-fluorobenzyl)-2-(N-methylamino)-9H-purine.

EXAMPLE 15

In a manner analogous to that described in Examples 1 to 12 it is also possible to obtain the 6-amino-2-(N,N-dimethylamino)-9-(2-fluorobenzyl)-9H-purine.

EXAMPLE 16

In a manner analogous to that described in Examples 1 to 12 it is also possible to obtain the 2-(N-ethylamino)-6-amino-9-(2-fluorobenzyl)-9H-purine.

EXAMPLE 17

In a manner analogous to that described in Example 1 it is also possible, by reacting 2-chloro-6-(N-methylamino)-9H-purine (Example 6) with 2,6-difluorobenzyl bromide, to obtain the 2-chloro-9-(2,6-diflurorbenzyl)-6-(N-methylamino)-9H-purine, which melts at from 194° to 195° (methanol/diethyl ether).

EXAMPLE 18

In a manner analogous to that described in Example 17 it is possible, by reacting 2-chloro-6-(N-methylamino)-9H-purine (Example 6) with 2-chlorobenzyl chloride, to obtain the 2-chloro-9-(2-chlorobenzyl)-6-(N-methylamino)-9H-purine, which melts at from 203° to 204° (N,N-dimethylformamide/diethyl ether).

EXAMPLE 19

In a manner analogous to that described in Example 2 it is possible, by reacting 2-chloro-9-(2,6-difluorobenzyl)-6-(N-methylamino)-9H-purine (Example 17) with N,N-dimethylamine, to obtain the 9-(2,6-difluorobenzyl)-2-(N,N-dimethylamino)-6-(N-methylamino)-9H-purine, which has a melting range of from 196° to 199° (methanol), the reaction mixture being heated at 140° for 24 hours.

EXAMPLE 20

In a manner analogous to that described in Example 2 it is possible, by reacting 2-chloro-9-(2-chlorobenzyl)-6-(N-methylamino)-9H-purine (Example 18) with N-methylamine, to obtain the 2,6-bis(N-methylamino)-9-(2-chlorobenzyl)-9H-purine, which has a melting range of from 151° to 152°, the reaction mixture being heated at 120° for 20 hours.

EXAMPLE 21

It is also possible to obtain the following compounds in a manner analogous to that described in Examples 1 to 20 using appropriate 2-chlorobenzyl-containing starting materials:

2-chloro-9-(2-chlorobenzyl)-6-(N,N-dimethylamino)-9H-purine; 9-(2-chlorobenzyl)-6-(N,N-dimethylamino)-2-(N-methylamino)-9H-purine; 2-amino-9-(2-chlorobenzyl)-6-(N,N-dimethylamino)-9H-purine; 2-(N-ethylamino)-9-(2-chlorobenzyl)-6-(N,N-dimethylamino)-9H-purine; 9-(2-chlorobenzyl)-2-(N-methylamino)-9H-purine; 9-(2-chlorobenzyl)-2-(N,N-dimethylamino)-9H-purine; 2,6-bis(N,N-dimethylamino)-9-(2-chlorobenzyl)-9H-purine; 2-amino-9-(2-chlorobenzyl)-6-(N-methylamino)-9H-purine; 9-(2-chlorobenzyl)-2-(N,N-dimethylamino)-6-(N-methylamino)-9H-purine; 2,6-diamino-9-(2-chlorobenzyl)-9H-purine; 6-amino-9-(2-chlorobenzyl)-2-(N-methylamino)-9H-purine; 6-amino-9-(2-chlorobenzyl)-2-(N,N-dimethylamino)-9H-purine; 2-(N-ethylamino)-6-amino-9-(2-chlorobenzyl)-9H-purine and 2-chloro-9-(2-chlorobenzyl)-9H-purine.

EXAMPLE 22

It is also possible to obtain the following compounds in a manner analogous to that described in Examples 1 to 20 using appropriate 2,6-difluorobenzyl-containing starting materials:

2-chloro-9-(2,6-difluorobenzyl)-6-(N,N-dimethylamino)-9H-purine; 9-(2,6-difluorobenzyl)-6-(N,N-dimethylamino)-2-(N-methylamino)-9H-purine; 2-amino-9-(2,6-difluorobenzyl)-6-(N,N-dimethylamino)-9H-purine; 2-(N-ethylamino)-9-(2,6-difluorobenzyl)-6(N,N-dimethylamino)-9H-purine; 9-(2,6-difluorobenzyl)-2-(N-methylamino)-9H-purine; 9-(2,6-difluorobenzyl)-2-(N,N-dimethylamino)-9H-purine; 2,6-bis(N,N-dimethylamino)-9-(2,6-difluorobenzyl)-9H-purine; 2-amino-9-(2,6-difluorobenzyl)-6-(N-methylamino)-9H-purine; 2,6-bis(N-methylamino)-9-(2,6-difluorobenzyl)-9H-purine; 2,6-diamino-9-(2,6-difluorobenzyl)-9H-purine; 6-amino-9-(2,6-difluorobenzyl)-2-(N-methylamino)-9H-purine; 6-amino-9-(2,6-difluorobenzyl)-2-(N,N-dimethylamino)-9H-purine; 2-(N-ethylamino)-6-amino-9-(2,6-difluorobenzyl)-9H-purine and 2-chloro-9-(2,6-difluorobenzyl)-9H-purine.

EXAMPLE 23

The following may also be obtained in a manner analogous to that described in Examples 1 to 22:

6-(N-acetylamino)-9-(2-fluorobenzyl)-2-(N-methylamino)-9H-purine; 6-(N-acetylamino)-9-(2-chlorobenzyl)-2-(N-methylamino)-9H-purine and 6-(N-acetylamino)-9-(2,6-difluorobenzyl)-2-(N-methylamino)-9H-purine.

EXAMPLE 24

Tablets each containing 50 mg of the active ingredient, for example 6-(N,N-dimethylamino)-9-(2-fluorobenzyl)-2-(N-methylamino)-9H-purine or a pharmaceutically acceptable salt thereof, can be produced as follows:

| Composition (for 10,000 tablets): | |
| --- | --- |
| active ingredient | 500.0 g |
| lactose | 500.0 g |
| potato starch | 352.0 g |
| gelatin | 8.0 g |
| talc | 60.0 g |
| magnesium stearate | 10.0 g |
| silicon dioxide (highly dispersed) | 20.0 g |
| ethanol | q.s. |

The active ingredient is mixed with the lactose and 292 g of potato starch, and the mixture is moistened with an alcoholic solution of the gelatin and granulated through a sieve. After the granulate has been dried, the remainder of the potato starch, the talc, the magnesium stearate and the highly dispersed silicon dioxide are mixed in and the mixture is compressed to form tablets each weighing 145.0 mg and containing 50.0 mg of active ingredient which, if desired, may be provided with dividing notches for finer adjustment of the dose.

EXAMPLE 25

Film-coated tablets each containing 200 mg of the active ingredient, for example 6-(N,N-dimethylamino)-9-(2-fluorobenzyl)-2-(N-methylamino)-9H-purine or a pharmaceutically acceptable salt thereof, can be produced as follows:

| Composition (for 500 tablets): | |
| --- | --- |
| active ingredient | 100.00 g |
| lactose | 100.00 g |
| corn starch | 70.00 g |
| talc | 8.50 g |
| calcium stearate | 1.50 g |
| hydroxypropylmethylcellulose | 1.18 g |
| shellac | 0.32 g |
| water | q.s. |
| dichloromethane | q.s. |

The active ingredient, the lactose and 40 g of the corn starch are mixed and moistened with a paste produced from 15 g of corn starch and water (with heating), and granulated. The granulate is dried, and the remainder of the corn starch, the talc and the calcium stearate are added and mixed with the granulate. The mixture is compressed to form tablets (weight: 560 mg) and the tablets are film-coated with a solution of the hydroxypropylmethylcellulose and the shellac in dichloromethane; final weight of the film-coated tablet: 563 mg.

EXAMPLE 26

In a manner analogous to that described in Examples 24 and 25 it is also possible to produce pharmaceutical preparations containing a different compound of formula I or a pharmaceutically acceptable salt thereof, for example according to Examples 1 to 23.

I claim:

1. A 9H-purine derivative of the formula $$
\begin{array}{c}
R_1 \\
| \\
N_1 \underset{2}{\overset{6}{\diagup}} \underset{}{\overset{5}{\diagdown}} N \\
R_2 - \underset{N}{\overset{}{\diagup}} \underset{3}{\overset{}{\diagdown}} \underset{4}{\overset{}{\diagup}} \underset{N}{\overset{9}{\diagdown}} \underset{|}{\overset{8}{\diagup}} \\
CH_2 - Ph
\end{array}
\qquad (I)
$$

in which Ph is 2-halophenyl or 2,6-dihalophenyl, wherein halo in each case is halogen having an atomic number of up to and including 35;

$R_1$ is amino, N-$C_1$–$C_4$alkylamino or N,N-di-$C_1$–$C_4$alkylamino; and $R_2$ is amino, N-$C_1$–$C_4$alkylamino or N,N-di-$C_1$–$C_4$alkylamino;

in free form or in form of a pharmaceutically acceptable salt thereof.

2. A compound according to claim 1 in which Ph is 2-fluorophenyl, 2-chlorophenyl or 2,6-difluorophenyl; $R_1$ is amino, N-$C_1$–$C_4$alkylamino or N,N-di-$C_1$–$C_4$alkylamino; and $R_2$ is amino, N-$C_1$–$C_4$alkylamino or N,N-di-$C_1$–$C_4$alkylamino; in free form or in form of a pharmaceutically acceptable salt thereof.

3. A compound according to claim 1 in which Ph is 2-fluorophenyl or 2,6-difluorophenyl; $R_1$ is N-$C_1$–$C_4$alkylamino or N,N-di-$C_1$–$C_4$alkylamino; and $R_2$ is amino, N-$C_1$–$C_4$alkylamino or N,N-di-$C_1$–$C_4$alkylamino; in free form or in form of a pharmaceutically acceptable salt thereof.

4. A compound according to claim 1 in which Ph is 2-fluorophenyl; $R_1$ is N,N-di-$C_1$–$C_4$alkylamino; and $R_2$ is amino or N-$C_1$–$C_4$alkylamino; in free form or in form of a pharmaceutically acceptable salt thereof.

5. A compound according to claim 1 in which Ph is 2-fluorophenyl; $R_1$ is N,N-di-$C_1$–$C_4$alkylamino; and $R_2$ is N-$C_1$–$C_4$alkylamino; in free form or in form of a pharmaceutically acceptable salt thereof.

6. A compound according to claim 1 being 6-(N,N-dimethylamino)-9-(2-fluorobenzyl)-2-(N-methylamino)-9H-purine or a pharmaceutically acceptable salt thereof.

7. A compound according to claim 1 being 2-amino-9-(2-fluorobenzyl)-6-(N-methylamino)-9H-purine or a pharmaceutically acceptable salt thereof.

8. A compound according to claim 1 being 2,6-bis(N-methylamino)-9-(2-fluorobenzyl)-9H-purine or a pharmaceutically acceptable salt thereof.

9. A compound according to claim 1 being 9-(2,6-difluorobenzyl)-2-(N,N-dimethylamino)-6-(N-methylamino)-9H-purine or a pharmaceutically acceptable salt thereof.

10. An anticonvulsive pharmaceutical preparation comprising an anticonvulsively effective amount of a compound according to claim 1 or of a pharmaceutically acceptable salt thereof, and at least one pharmaceutically acceptable adjunct.

11. A method for treating convulsions in a subject in need of such treatment which comprises administering to such subject an anticonvulsively effective amount of a compound according to claim 1 or of a pharmaceutically acceptable salt thereof.

12. A method according to claim 11 for treating epilepsy in a subject in need of such treatment which comprises administering to such subject an antiepileptically effective amount of a compound according to claim 1 or of a pharmaceutically acceptable salt thereof.

* * * * *